United States Patent [19]

Yokota et al.

[11] Patent Number: 5,560,470
[45] Date of Patent: Oct. 1, 1996

[54] MEANS FOR DISCRIMINATING SIDES OF TEST STRIPS IN AUTOMATED ANALYZER

[75] Inventors: Hiroshi Yokota; Keiji Takahashi, both of Hiratsuka, Japan

[73] Assignee: Bayer Corporation, Elkhart, Ind.

[21] Appl. No.: 422,245

[22] Filed: Apr. 14, 1995

[30] Foreign Application Priority Data

May 10, 1994 [JP] Japan .................... 6-119737

[51] Int. Cl.$^6$ ................................. B65G 47/24
[52] U.S. Cl. ........................... 198/395; 198/399
[58] Field of Search .................. 414/755, 763, 414/773, 783, 797; 422/58, 63, 64, 65, 67, 269, 297, 303; 198/395, 399

[56] References Cited

U.S. PATENT DOCUMENTS

| | | | |
|---|---|---|---|
| 3,472,356 | 10/1969 | Reppert | 414/763 |
| 4,050,574 | 9/1977 | Chenevard et al. | 414/763 |
| 4,172,513 | 10/1979 | Bradstreet et al. | 414/755 |
| 4,242,038 | 12/1980 | Santini et al. | 414/755 |
| 4,425,075 | 1/1984 | Quinn | 414/755 |
| 4,457,662 | 7/1984 | Ireland et al. | 414/763 |
| 4,806,071 | 2/1989 | Sartorio | 414/797 |
| 4,972,935 | 11/1990 | Gross et al. | 198/395 |
| 5,097,938 | 3/1992 | Grüner et al. | 198/399 |
| 5,108,513 | 4/1992 | Muller et al. | 414/755 |
| 5,236,078 | 8/1993 | Gross et al. | 198/399 |
| 5,298,425 | 3/1994 | Kuhn et al. | 198/399 |

*Primary Examiner*—Karen B. Merritt
*Assistant Examiner*—Douglas Hess
*Attorney, Agent, or Firm*—Roger N. Coe

[57] ABSTRACT

Disclosed is a device for discriminating the right sides of test strips in an automated analyzer for arranging the test strips such that the right sides thereof may face in one direction, which comprises: suction holes formed on a transportation stage to be aligned in the direction orthogonal to the direction that the test strips are moved, at the positions corresponding to the intervals between test pads impregnated with reagents of the test strip; and suction holes formed on a turntable disposed subsequent to the transportation stage, at the positions corresponding to the intervals between the test pads impregnated with reagents of the test strip.

1 Claim, 4 Drawing Sheets

MEANS FOR DISCRIMINATING SIDES OF TEST STRIPS IN AUTOMATED ANALYZER

BACKGROUND OF THE INVENTION

This invention relates to a means for discriminating the right sides of test strips in an automated analyzer, more specifically to a means for discriminating the right sides of test strips in an automated analyzer, which discriminates the right sides of test strips by means of air for arranging test pads such that the right sides thereof may face in one direction.

In the prior art, a test strip has been frequently used for testing a plurality of analysis items (analytes) of a specimen such as urine easily and simply. As shown in FIG. 6, in a test strip 1, a plurality of test pads 3 impregnated with reagents are pasted on one end portion of a long and slender strip 2 made of plastic, and the other end portion is a holding portion 4. The respective specimen components are analyzed by dipping the test strip 1 in a specimen to wet the test pads 3 and measure coloration intensities of the test pads 3 at a light measuring portion of an analyzer.

In order to carry out the above operations automatically, the test strips 1 should be arranged such that the right sides of the test pads 3 face in one direction by the time the test strips 1 are dipped in the specimens and supplied to the light measuring portion. The test strips 1 are contained in a test strip bottle such that the holding portions 4 may face to an opening, but the sides thereof do not face in one direction, i.e., the test pads 3 face in different directions. In order to realize full automation, it is required to incorporate a device for arranging the test strips 1 such that the right sides of the test pads 3 face in one direction in an analyzer.

SUMMARY OF THE INVENTION

An object of the present invention is to provide a means for discriminating the right sides of test strips in an automated analyzer, by which the right sides of test pads of test strips can securely be discriminated, the trouble of arranging the test strips beforehand such that the right sides thereof may face in one direction can be eliminated and full automation can be realized if the means of the present invention is employed in, for example, an automated analyzer in which a test strip bottle containing test strips is set as such and the test strips can directly be picked up from the test strip bottle.

As shown in FIG. 1 to FIG. 3, the means for discriminating the right sides of test strips 1 in an automated analyzer for arranging the test strips 1 such that the right sides thereof may face in one direction of the present invention comprises:

suction holes 15 formed on a transportation stage 11 to be aligned in the direction orthogonal to the direction that the test strips 1 are moved, at the positions corresponding to the intervals between test pads 3 impregnated with reagents of the test strip 1; and suction holes 17 formed on a turntable 16 disposed subsequent to the transportation stage 11, at the positions corresponding to the intervals between the test pads 3 impregnated with reagents of the test strip 1.

DESCRIPTION OF THE PREFERRED EMBODIMENTS

In the following, the present invention is explained in detail.

Figure 4:
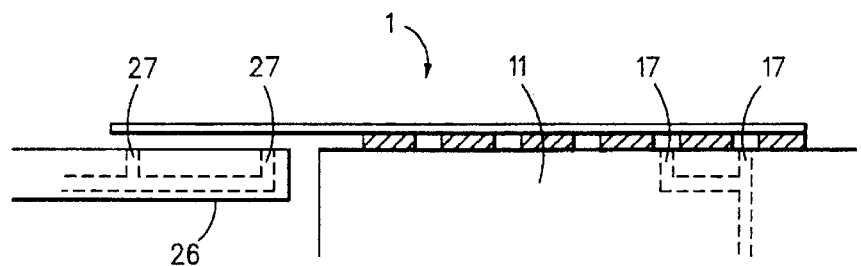
FIG. 4 is an illustrative view of the means for discriminating the right sides of test strips.
Figure 5:
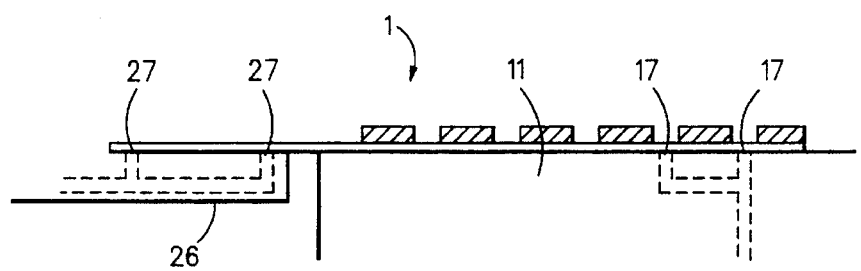
FIG. 5 is an illustrative view of the means for discriminating the right sides of test strips.
Figure 6:
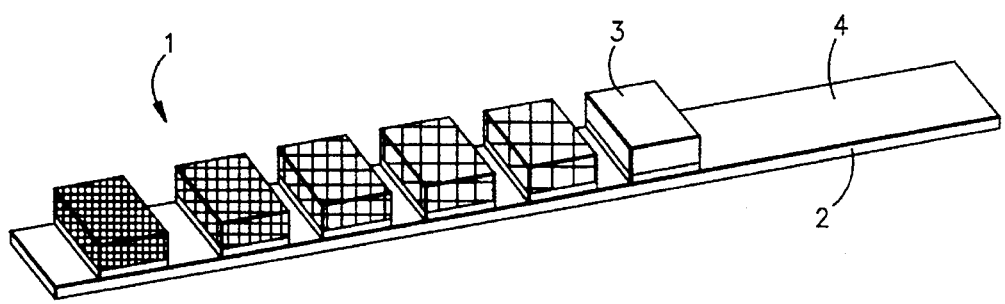
FIG. 6 is a perspective view of a test strip.

The suction holes 15 and 17 on the transportation stage 11 and the turntable 16 are formed at the positions corresponding to the intervals of the test pads 3 of the test strip 1 pushed by push bars 13. When the wrong side of the test strip 1 faces upward, the suction holes 17 are not blocked up as shown in FIG. 4 so that a vacuum degree is not increased by suction. On the other hand, when the right side of the test strip 1 faces upward, the suction holes 17 are blocked up as shown in FIG. 5 so that a vacuum degree is increased. Thus, by sucking the test strip 1 and measuring the vacuum degree, the right side of the test strip 1 can be discriminated easily.

The right side of the test strip 1 is discriminated by the suction holes 15 formed on the transportation stage 11 and the suction holes 17 formed on the turntable 16. Further, when it is judged twice on the turntable 16 that the wrong side of the test strip 1 faces upward, an analyzer is stopped, whereby the test strip 1 with the wrong side facing upward is not transported to a next dipping step.

EXAMPLES

One embodiment of the means for discriminating the right sides of test strips in an automated analyzer of the present invention is described in detail by referring to the drawings.

Figure 1:
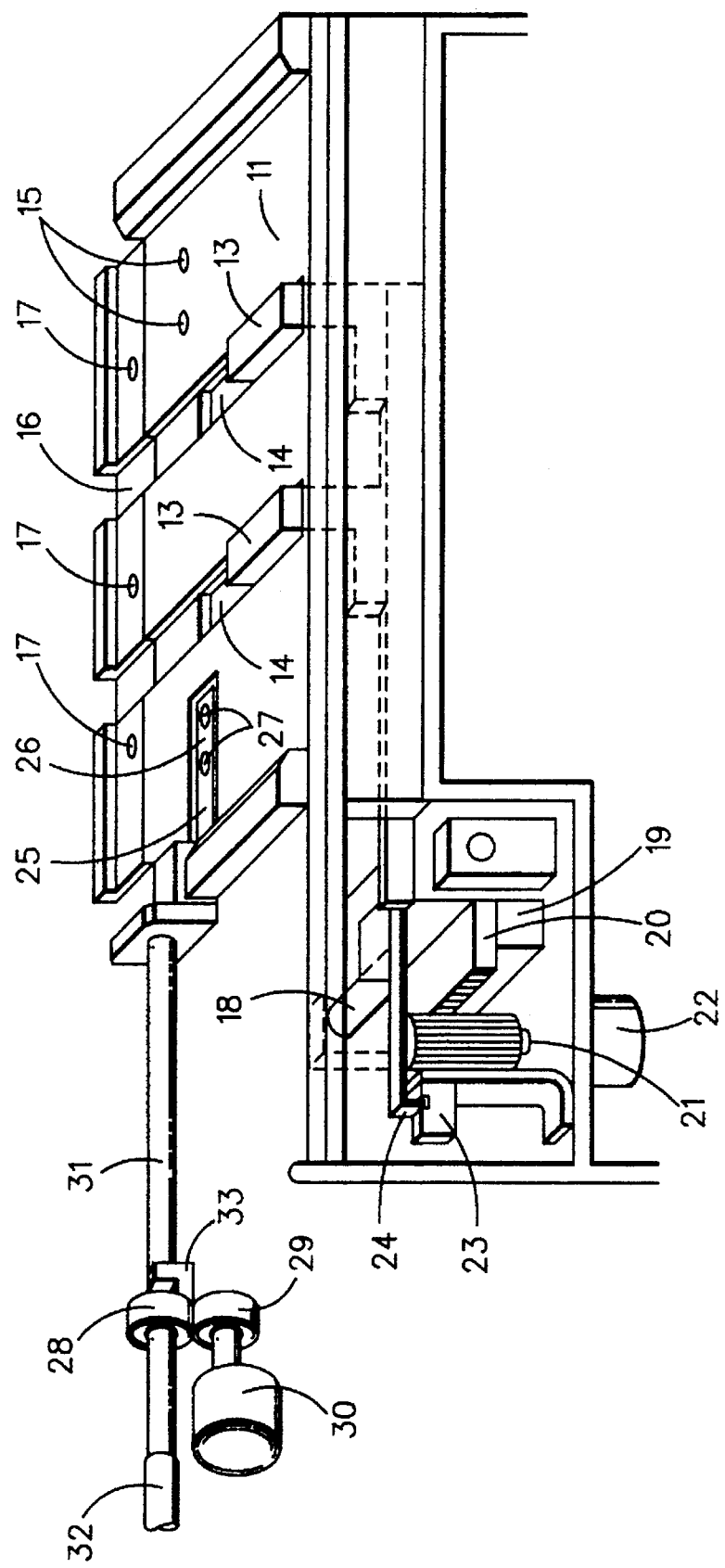
FIG. 1 is a perspective view showing the means for discriminating the right sides of test strips of the present invention.
Figure 2:
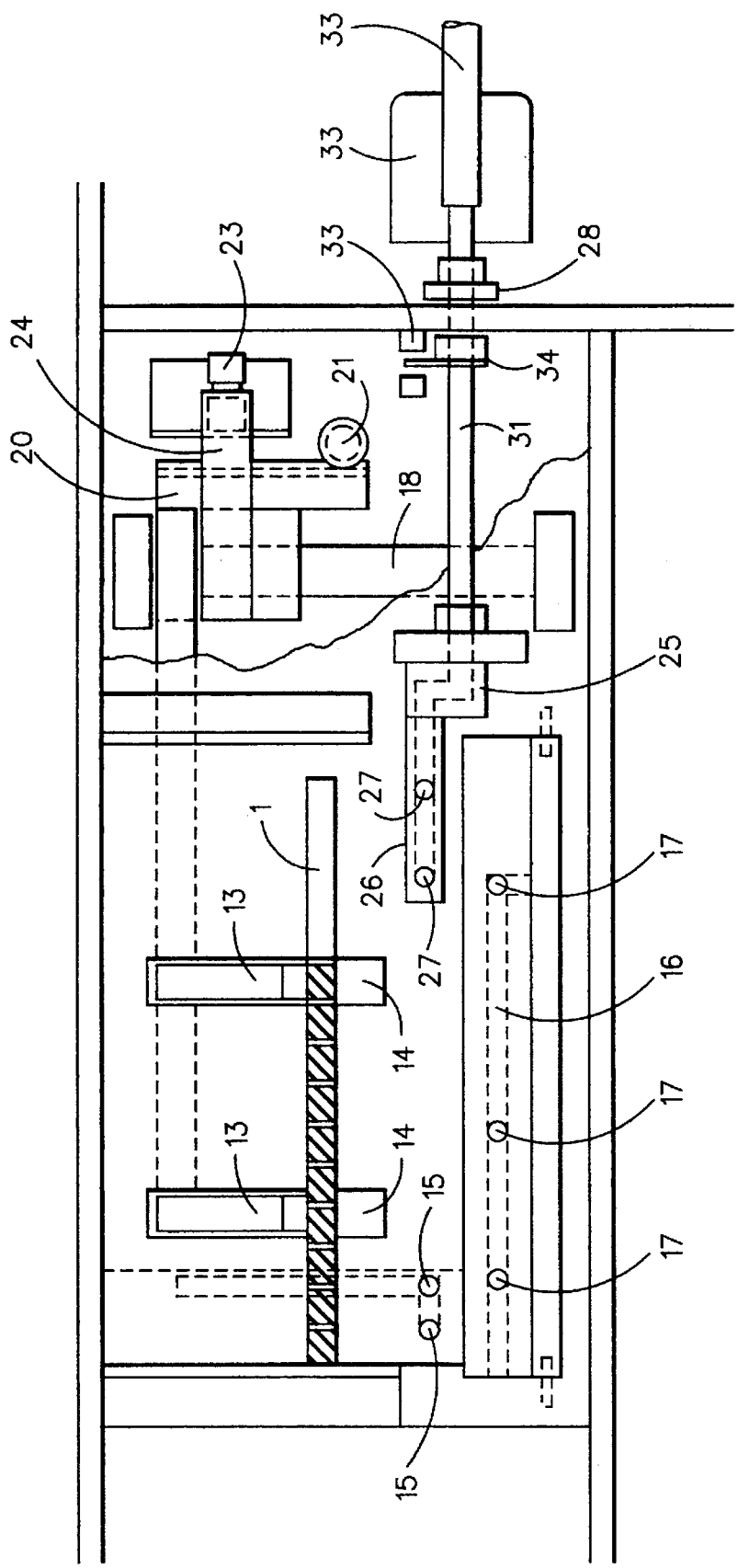
FIG. 2 is a plane view showing the means for discriminating the right sides of test strips of the present invention.
Figure 3:
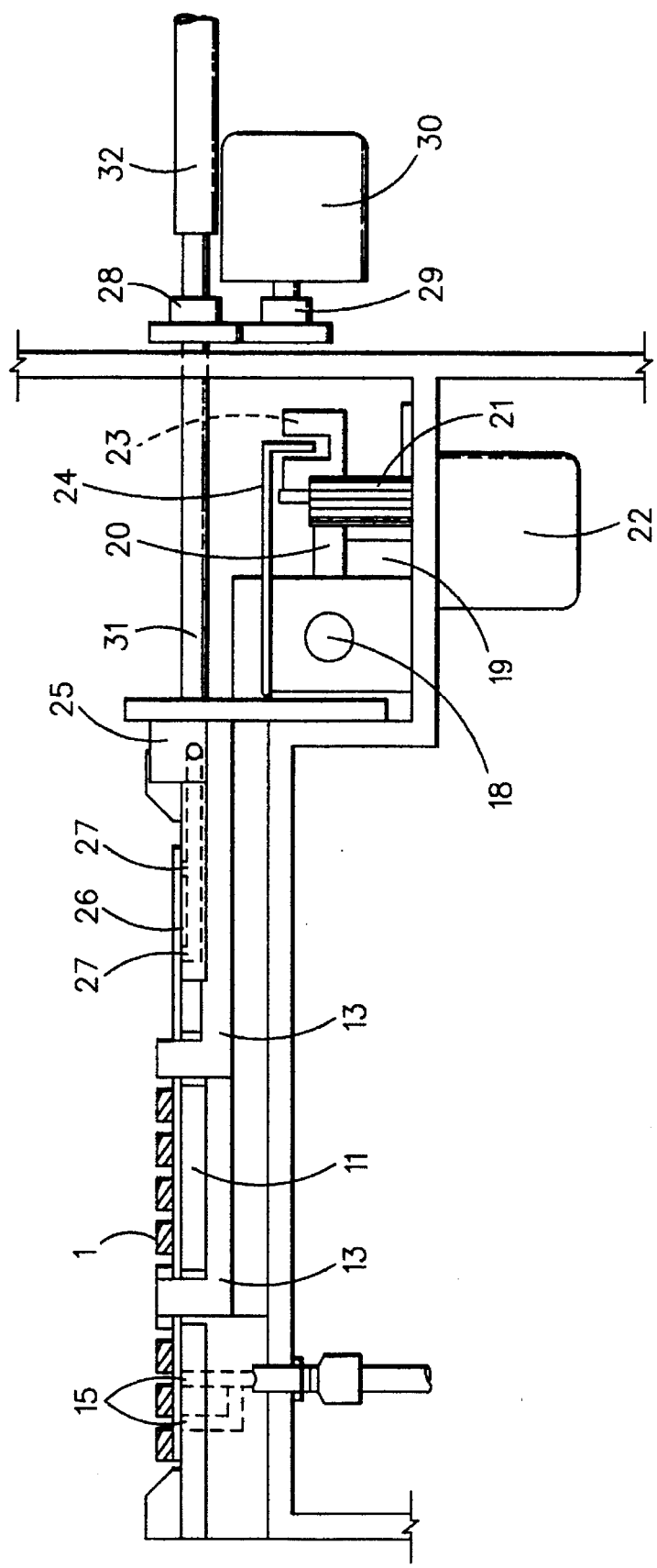
FIG. 3 is a side view showing the means for discriminating the right sides of test strips of the present invention.

As shown in FIG. 1 to FIG. 3, on the transportation stage 11 to which the test strip 1 picked up from a test strip bottle by being adsorbed to an air chuck is supplied, openings 14 are formed such that the push bars 13 pushing the test strip 1 are movable. On the transportation stage 11, two of the suction holes 15 connected to a vacuum pump not shown in the figures are formed to be aligned in the direction orthogonal to the direction that the test strip 1 pushed by the push bars 13 is moved on the transportation stage 11, at the positions corresponding to the intervals between the test pads 3 of the test strip 1.

Three of the suction holes 17 on the turntable 16 are formed to be aligned in the direction orthogonal to the direction that the test strip 1 pushed by the push bars 13 is moved on the transportation stage 11, at the positions corresponding to the intervals between the test pads 3 of the test strip 1. The suction holes 17 have roles of discriminating the right side of the test strip 1 and holding the test strip 1 by adsorption such that the test strip 1 may not be displaced when it is transported to a next dipping step.

The push bars 13 are mounted on a movable member 19 which moves on a linear shaft 18. The movable member 19 is connected to a motor 22 via a rack 20 and a gear 21. A limit switch 23 and a flag 24 mounted on the movable member 19 are provided for determining a stop position of the test strip 1.

In a L-shaped overturning device 25, two suction holes 27 are formed on an arm portion 26. The suction holes 27 are aligned in a straight line with the suction holes 15 formed on the transportation stage 11 in the direction orthogonal to the direction that the test strip 1 is moved. On the overturning device 25 is mounted a hollow rotary shaft 31 connected to a motor 30 via a gear 28 and a gear 29. The other end of the rotary shaft 31 is connected to a vacuum pump not shown in the figures via a suction tube 32.

The turntable 16 disposed after (subsequent to) the transportation stage 11 is disposed at the position corresponding to the location of the arm portion 26 when the overturning device 25 is turned 180° round the rotary shaft 31. A limit switch 33 and a flag 34 mounted on the rotary shaft 31 are provided for stopping the overturning device 25 at the position when it is turned 180°.

In the following, operations of discriminating right sides of the means for discriminating the right sides of test strips in an automated analyzer of the present invention are described in detail.

The test strip 1 picked up from the test strip bottle by being adsorbed to an air chuck is supplied on the transportation stage 11. Thereafter, the test strip 1 is pushed by the push bars 13 by actuating the motor 22 to be conveyed to the suction holes 15 on the transportation stage 11, and the motor 22 is stopped.

Then, the test strip 1 is sucked instantaneously to discriminate the right side of the test strip 1. When a specific vacuum degree is obtained, a detector not shown in the figures gives a signal that the right side of the test strip 1 faces upward. Then, the test strip 1 is pushed by the push bars 13 by actuating the motor 22 to be transported to the turntable 16.

When the specific vacuum degree is not obtained and the detector gives a signal that the wrong side of the test strip 1 faces upward, the test strip 1 is adsorbed (held) by the overturning device 25, the overturning device 25 is turned 180° by actuating the motor 30, and the test strip 1 is placed on the turntable 16 such that the right side thereof faces upward.

Then, the test strip 1 is sucked instantaneously also on the turntable 16 to discriminate the right side of the test strip 1. When the detector gives a signal that the wrong side of the test strip 1 faces upward, the test strip 1 is returned from the turntable 16 to the transportation stage 11 by turning the overturning device 25 180° in a reverse direction by actuating the motor 30, and the right side of the test strip 1 is made face upward. After suction of the overturning device 25 is stopped, the test strip 1 is pushed by the push bars 13 by actuating the motor 22 to be conveyed to the turntable 16.

On the turntable 16, the test strip 1 is sucked again instantaneously to discriminate the right side of the test strip 1. When the detector gives a signal that the wrong side faces upward, operations of the analyzer is interrupted. When the detector gives a signal that the right side of the test strip 1 faces upward, the test strip 1 is conveyed to a next Lest strip dipping step by lowering the turntable 16 by driving a motor not shown in the figures while the test strip 1 is adsorbed on the turntable 16. A next test strip is supplied on the transportation stage 11, and the operations described above are repeated.

According to the present invention, the right sides of test strips on which reagent portions are present can securely be discriminated, the trouble of arranging the test strips beforehand such that the right sides thereof may face in one direction can be eliminated and full automation can be realized if the means of the present invention is employed in, for example, an automated analyzer in which a container containing test strips is set as such and the test strips can directly be picked up from the container.

We claim:

1. A device for discriminating the measurable side of a test strip in an automated analyzer and arranging the test strip such that the measurable side thereof faces in a proper direction for the analyzer, which comprises:

suction holes formed on a transportation stage of said device, said suction holes being aligned in a direction orthogonal to a direction that the test strip is moved and being located at positions corresponding to intervals between test pads impregnated with reagents on said test strip;

suction holes formed on a turntable of said device disposed subsequent to the transportation stage, said suction holes on the turntable being at positions corresponding to the intervals between the test pads on said test strip; and means for rotating said turntable to turn the test strip over if the measurable side thereof is not properly positioned for the automated analyzer.

* * * * *